July 18, 1967 E. D. HUDSON Plant Pat. 2,753
AZALEA PLANT
Filed May 23, 1966
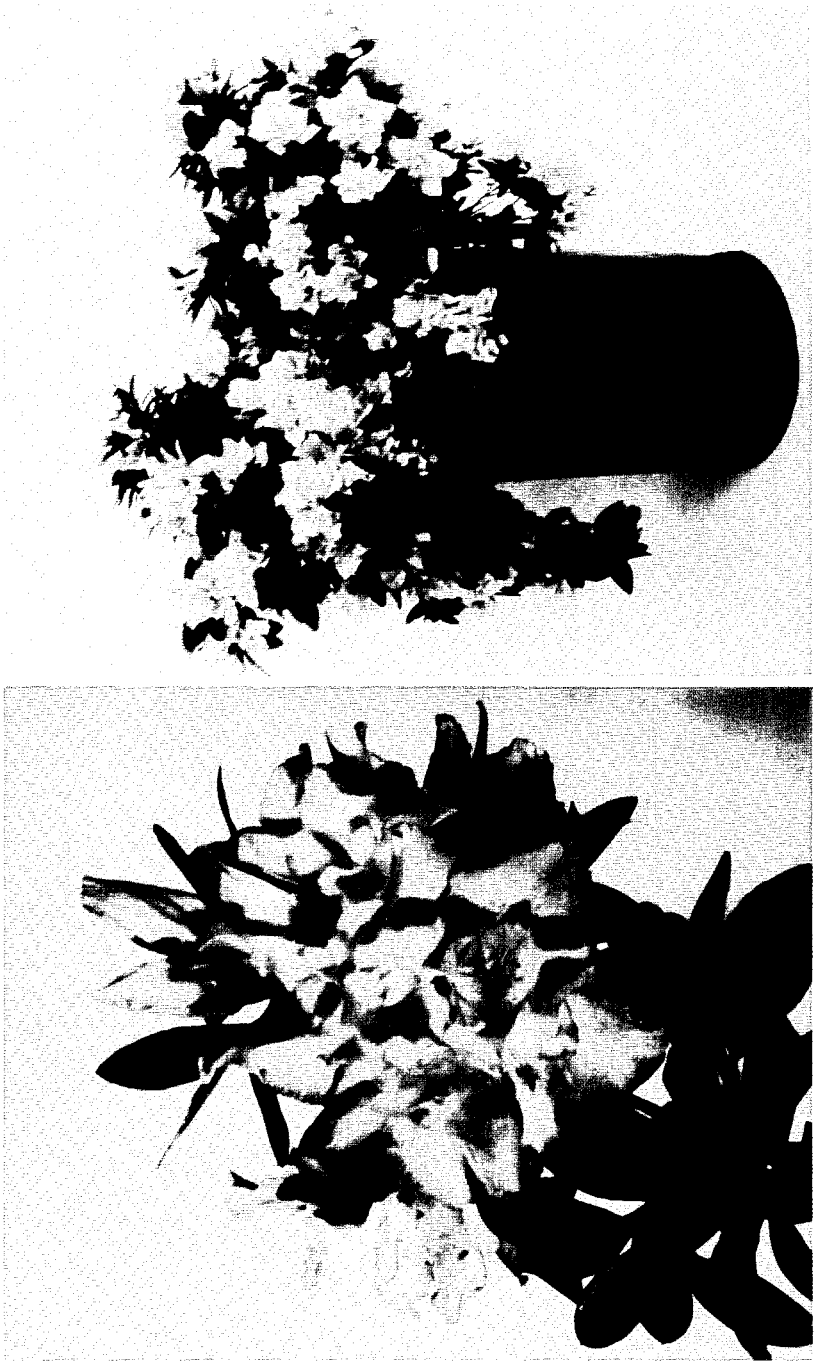
INVENTOR.
EARL D. HUDSON,
By Edmond F. Shanahan
ATTORNEY.

United States Patent Office

Plant Pat. 2,753
Patented July 18, 1967

2,753
AZALEA PLANT

Earl D. Hudson, Hemet, Calif., assignor to Monrovia Nursery Co., Azusa, Calif., a corporation of California Filed May 23, 1966, Ser. No. 552,353
1 Claim. (Cl. Plt.—56)

The present invention relates to a new and distinct variety of azalea plant.

The plant is characterized as to novelty by the unique coloring of its flowers, both in shade and in pattern, as illustrated and described herein; by its abundant rich green foliage; by its ability to grow and flower in full sun or light shade; and by its compact, densely branched habit of growth.

I discovered the original plant as a seedling originating in December 1959, and first flowering in December 1961. It will not come true from seeds; however, it has been propagated by grafting and cutting. The plant is reproduced asexually and asexually only.

A plant and flower of the new variety are shown in full color in the accompanying illustration.

A detailed description of the new variety follows, and to facilitate identification of the importont colors, the color terminology adopted by the British Horticultural Color Charts has been followed. (Reference is to "Horticultural Color Charts" issued by the British Color Council in two volumes, in collaboration with the Royal Horticultural Society, copyright by Robert F. Wilson, published 1938–41.)

*The plant*

Parentage: Seedling resulting from open pollenation.
*Pollen parent.*—Unknown.
*Seed parent.*—Azalea "Laughing Waters," an unpatented variety.

Growth: The plant is of a moderately vigorous, compact, semi-upright habit of growth, well-clothed with foliage. The ultimate height of the plant is not known, but under normal conditions it should reach a height of from 3 to 4 feet, with a spread of 5 to 6 feet at maturity.

Branches: New growth is a light green, gradually changing to light brown as the branch matures. The new growth is densely covered with white hairs which gradually change to brown as the branch matures.

Growth habit: Branching starts just above ground level, and has a tendency to be spreading.

Foliage: The leaves are of good substance and are glossy.

Shape: The leaves are best described as being obovate to oblanceolate. Margins are entire and ciliate. Apex of the leaf is mucronulate; base is attenuate. New leaves are Scheeles Green 860/1 on the upper surface and Scheeles Green 860/3 on the underside. Mature leaves are slightly darker than Spinach Green o960 on the upper surface and 1960/2 on the underside. Both upper and under surfaces of the leaves are remotely strigose hairy.

Size: Leaves range from 1¾ to 2½ inches in length, and from ⅝ to 1⅛ inches in width. Petiole is 5/16 inches in length.

Arrangement: Leaves are alternate on the branches.

Veins: The midrib on the upperside and the underside of the leaf blade is strigose hairy and is lighter in color than the leaf blade.

*The flower*

The plant sets an occasional bloom from October until late January, when it produces its heaviest bloom, lasting through February and into early March. It will then continue to produce an occasional bloom until late April.

Form: Flowers are of the single hose-in-hose type, with an occasional flower being a semi-double hose-in-hose type. Flowers have a natural spread of 3 to 3½ inches.

Petals: Petals are ten in number, placed in two ranks of five.

Color: The base of the corolla tube is white, gradually shading up to the petal lobes, which are Solferino Purple 26/2. The standard petal and the two wing petals are blotched with Spiraea Red o25.

I claim:

A new and distinct variety of azalea plant, substantially as herein described and illustrated, and characterized particularly as to novelty by the unique coloring of its flowers, both in shade and in pattern; by its abundant, rich green foliage; by its ability to grow and flower in full sun or light shade; and by its compact, densely branched habit of growth.

No references cited.

ABRAHAM G. STONE, *Primary Examiner.*

ROBERT E. BAGWILL, *Examiner.*